United States Patent [19]

Frazier

[11] Patent Number: 4,734,521

[45] Date of Patent: Mar. 29, 1988

[54] PROCESS FOR MAKING BETA, GAMMA-UNSATURATED ESTER, CARBAMATES AND SULFONAMIDES

[75] Inventor: Kevin A. Frazier, Midland, Mich.

[73] Assignee: The Dow Chemical Company, Midland, Mich.

[21] Appl. No.: 81,923

[22] Filed: Aug. 5, 1987

Related U.S. Application Data

[63] Continuation-in-part of Ser. No. 798,547, Nov. 15, 1985, abandoned.

[51] Int. Cl.$^4$ .................................. C07C 125/065
[52] U.S. Cl. .................................. 560/157; 560/24; 560/221; 560/225; 560/240; 564/90; 564/92; 564/98; 564/99
[58] Field of Search .............. 560/157, 24, 221, 225, 560/240; 564/90, 92, 98, 99

[56] References Cited

U.S. PATENT DOCUMENTS

| | | | |
|---|---|---|---|
| 2,030,835 | 2/1936 | Cox | 560/240 |
| 2,629,735 | 2/1953 | Cottle | 560/240 |
| 3,250,813 | 5/1966 | Stephenson | 260/614 |
| 3,493,617 | 2/1970 | Shryne | 564/474 |
| 3,510,511 | 5/1970 | Conseiller | 560/240 |
| 3,970,705 | 7/1976 | Taylor | 260/614 |
| 4,466,922 | 8/1984 | Wertz | 560/240 |

OTHER PUBLICATIONS

Warren, J. Org. Chem. 23, pp. 1666–1668 (1958).
Roberts, "Basic Principles of Organic Chemistry," pp. 407–411 (1964).
Mortimer, "Chemistry a Conceptual Approach", pp. 431–451 (1967).
Olah et al., Journal of the American Chemical Society, 94, p. 7448 (1972).
Journal of Organic Chemistry, 23, 1666 (1958), "Homogeneous Metal Salt Catalysis in Organic Reactions. III. The Preparation of Allyl Ethers by Allyl Transfer Reactions[1,2]".

*Primary Examiner*—Michael L. Shippen

[57] ABSTRACT

$\beta,\gamma$-Unsaturated non-epoxide ethers react with carboxylic acids, carbamates or sulfonamides to form the corresponding $\beta,\gamma$-unsaturated esters, carbamates or sulfonamides. The reaction is catalyzed with sulfonated polystyrene beads and is promoted by copper (I) chloride.

18 Claims, No Drawings

PROCESS FOR MAKING BETA, GAMMA-UNSATURATED ESTER, CARBAMATES AND SULFONAMIDES

CROSS REFERENCE TO RELATED APPLICATION

This application is a continuation-in-part of Applicant's copending application, Ser. No. 798,547 filed Nov. 15, 1985, now abandoned.

BACKGROUND OF THE INVENTION

This invention relates to the processes for making of $\beta,\gamma$-unsaturated esters, carbamates and sulfonamides. More particularly, it relates to the catalyzed reaction of $\beta,\gamma$-unsaturated ethers to form the desired ester, carbamate or sulfonamide.

The $\beta,\gamma$-unsaturated esters, carbamates and sulfonamides are useful as cross-linkable monomers, and reaction intermediates.

Conventionally, $\beta,\gamma$-unsaturated esters, carbamates and sulfonamides are produced by reacting a $\beta,\gamma$-unsaturated halide with an alkali metal salt of an organic radical, thereby forming the desired $\beta,\gamma$-unsaturated ester, carbamate or sulfonamide and disadvantageously coproducing an alkali metal halide salt.

It would be desirable to have a salt-free process for the preparation of $\beta,\gamma$-unsaturated esters, carbamates or sulfonamides. It would be further desirable if the salt-free process also did not consume alkali metal salts of organic radicals.

SUMMARY OF THE INVENTION

The invention is a process wherein no salt is formed for making $\beta,\gamma$-unsaturated esters, carbamates and sulfonamides which comprises contacting a $\beta,\gamma$-unsaturated non-epoxide ether with an organic compound selected from the group consisting of organic carboxylic acids, organic carbamates and organic sulfonamides in the presence of a catalytic amount of a catalyst, the catalyst being either (1) a sulfonic acid, (2) sulfuric acid, (3) $BF_3$, (4) $AlCl_3$, (5) $BF_3.(CH_3CH_2)_2O$, or (6) a combination thereof; and in the further presence of a promoting amount of a promoter selected from the group consisting of copper (I) salts and cobalt (II) salts under conditions sufficient to form the corresponding $\beta,\gamma$-unsaturated ester, carbamate or sulfonamide.

These $\beta,\gamma$-unsaturated esters, carbamates and sulfonamides are useful as cross-linkable monomers and reaction intermediates.

DETAILED DESCRIPTION OF THE INVENTION

The present invention is a process for making $\beta,\gamma$-unsaturated esters, carbamates and sulfonamides. This process can be represented by the following formula in one embodiment

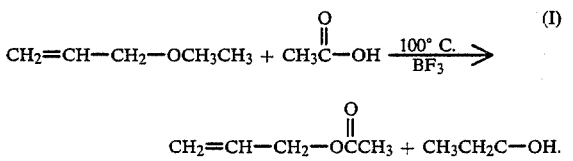

The $\beta,\gamma$-unsaturated non-epoxide ethers can be any non-epoxide ether possessing an ether oxygen and unsaturation between a carbon atom $\gamma$ from the ether oxygen and a carbon atom $\beta$ from the ether oxygen. An example of such a $\beta,\gamma$-unsaturated non-epoxide ether can be represented by the formula

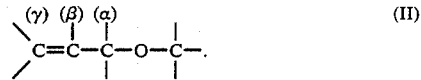

In the above formula, the carbon atoms adjacent to the oxygen atom are not part of an epoxide moiety. The unsaturation between the $\beta$ and $\gamma$ carbons may be a double bond, aryl bond or triple bond, with double bonds and aryl bonds being preferred and double bonds being most preferred. The $\beta,\gamma$-unsaturated ethers, organic acids and diluents may have one or more substituents and/or one or more heteroatoms. These substituents and heteroatoms do not react under the conditions of the invented process to a degree sufficient to prevent the formation of $\beta,\gamma$-unsaturated esters, carbamates or sulfonamides.

Preferably, the $\beta,\gamma$-unsaturated non-epoxide ethers are allyl ethers and benzyl ethers, most preferably allyl ethers. Allyl ethers include the moiety $CH_2=CHCH_2-O-$. Benzyl ethers include the moiety

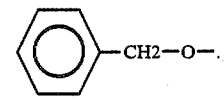

Benzyl ethers include benzyl methyl ether, benzyl ethyl ether and benzyl propyl ether. Allyl ethers include allyl methyl ether, allyl ethyl ether and allyl benzyl ether. The most preferred allyl ether is allyl methyl ether.

The organic carboxylic acids can be any organic molecule possessing a carboxylic acid substituent. Preferably, the organic carboxylic acid is acetic acid, acrylic acid and methacrylic acid. Most preferably, the organic carboxylic acid is acetic acid.

The organic carbamate can be any organic molecule possessing a carbamic acid substituent having N—H moiety. Preferably, the organic carbamate is methyl carbamate, ethyl carbamate, or N-methyl ethyl carbamate. Most preferably, the organic carbamate is N-methyl ethyl carbamate or methyl carbamate.

The organic sulfonamide can be any organic molecule possessing a sulfonamide with a N—H moiety. Preferably, the organic sulfonamide is benzene sulfonamide.

Catalysts useful in the practice of this invention include sulfonic acids, $BF_3$, $AlCl_3$, $BF_3.(CH_3CH_2)_2O$, sulfuric acid or some combination thereof. Sulfonic acids useful in the practice of this invention are represented by the formula $RSO_3H$ in which R is a monovalent organic moiety such as alkyl or aryl. It is preferred to use sulfonic acids as catalysts. It is more preferred to use p-toluene sulfonic acid, methane sulfonic acid or sulfonated polystyrene beads. It is most preferred to use sulfonated polystyrene beads as catalyst.

Any amount of catalyst which will catalyze the process of making $\beta,\gamma$-unsaturated esters, carbamates and sulfonamides is useful in the practice of this invention. The amount of catalyst preferred will depend on the different reaction conditions and reactants. When the catalyst is homogeneous, it is preferred that the mole ratio of acid to $\beta,\gamma$-unsaturated non-epoxide ether is between about 1:2 and 1:200. When the catalyst is heterogeneous as when it is sulfonated polystyrene beads, it is preferred the catalyst levels are between about 50 g of catalyst per mole of $\beta,\gamma$-unsaturated non-epoxide ether and about 150 g of catalyst per mole of $\beta,\gamma$-unsaturated non-epoxide ether. It is most preferred that, when using a heterogeneous catalyst such as sulfonated polystyrene beads, the catalyst level be about 100 g of catalyst per mole of $\beta,\gamma$-unsaturated ether.

The reactants are contacted in the presence of a promoting amount of a promoter. The promoter is selected from the group consisting of copper (I) salts and cobalt (II) salts. The most preferred promoter is copper (I) chloride. These promoters may be provided in any manner such as generation in situ.

Preferably, the promoter is present in a ratio of equivalents of promoter to equivalents of catalyst between about 1:1 and about 1:10, more preferably 1:5.

The reactants can be combined in any order and in any relative amount. Preferably, the mole ratio of $\beta,\gamma$-unsaturated ether to acid is less than about 100:1, more preferably less than about 50:1, even more preferably less than about 20:1 and most preferably less than about 10:1. Preferably, the mole ratio of $\beta,\gamma$-unsaturated non-epoxide ether to acid is greater than about 2:1, more preferably greater than about 5:1 and most preferably greater than about 7:1. The contact may disadvantageously take place in the presence of an unreactive diluent such as xylene. Unreactive means does not react under the reaction conditions to a degree sufficient to prevent the formation of the $\beta,\gamma$-unsaturated ester, carbamate or sulfonamide products.

The contact occurs under conditions sufficient to form the desired $\beta,\gamma$-unsaturated ester, carbamate or sulfonamide. Typically, the reaction is practiced in a stainless steel reactor.

The contact is at a temperature sufficient to form the $\beta,\gamma$-unsaturated ester, carbamate or sulfonamide. Preferably, the temperature of the contact is below about 200° C., more preferably below about 150° C. Preferably, the temperature of the contact is above about 25° C., more preferably above about 50° C. and most preferably above about 70° C.

The contact is at a pressure sufficient to form the $\beta,\gamma$-unsaturated ester, carbamate or sulfonamide. Preferably, the pressure is between about the generated pressure and about 100 psig (670 kPa). The generated pressure is the pressure generated by the reaction mixture itself. Most preferably, the pressure is about the generated pressure.

The contact should be until the reaction has proceeded to an acceptable degree. Preferably, contact is until at least about 30 mole percent of the $\beta,\gamma$-unsaturated non-epoxide ether is consumed, more preferably at least about 50 mole percent, most preferably at least about 60 mole percent.

Selectivities are dependent upon reactants and conditions. Preferred selectivities to $\beta,\gamma$-unsaturated ester, carbamate or sulfonamide are at least about 50 mole percent based on the reacted $\beta,\gamma$-unsaturated non-epoxide ether, more preferably at least about 70 mole percent and most preferably at least about 90 mole percent.

The contact produces the desired $\beta,\gamma$-unsaturated ester and carbamate or sulfonamide. Carbamates and sulfonamide products include both the mono and the di $\beta,\gamma$-unsaturated products. The particular reaction products are dependent upon the particular reactants and conditions.

This invention is further illustrated by the following non-limiting examples.

EXAMPLE 1

Into a 0.3-liter stainless steel reactor are placed 7.2 g (0.100 mole) of allyl methyl ether, 30.3 g of (0.500 mole) of acetic acid, 1 g (0.0101 mole) of copper (I) chloride and 5 g of sulfonated polystyrene beads. The reactor is sealed, purged and heated to 100° C. for 30 minutes. The reactor is cooled to room temperature, and opened. As a gas chromatograph standard, 5 ml (0.04088 mole) of m-xylene is added and the reaction mixture is analyzed by gas chromatography to be as set forth below in Table I.

TABLE I

| Product | moles | Normalized Results* |
|---|---|---|
| allyl methyl ether | 0.0283 | 0.283 |
| allyl acetate | 0.0586 | 0.586 |
| allyl alcohol | 0.0021 | 0.021 |
| methyl acetate | 0.0869 | 0.869 |
| methanol | 0.0014 | 0.014 |
| acetic acid [1] | — | — |

*Normalized results are moles of product divided by moles of allyl methyl ether added.
[1] Not calibrated.

The selectivity of allyl methyl ether to allyl acetate is 81.7 mole percent.

EXAMPLE 2

Example 1 is repeated except using 17.95 g (0.248 mole) of allyl methyl ether, 30.8 g (0.513 mole) of acetic acid, 1 g (0.0101 mole) of copper (I) chloride, 10 g of sulfonated polystyrene beads, and 5 ml (0.04088 mole) of m-xylene as a gas chromatograph standard. The reactor is heated to 100° C. for 1 hour. The results of the gas chromatograph analysis of the reaction products are shown in Table II.

TABLE II

| Product | Moles | Normalized Results* |
|---|---|---|
| allyl methyl ether | 0.0954 | 0.385 |
| allyl acetate | 0.0983 | 0.397 |
| allyl alcohol | 0.0132 | 0.053 |
| diallyl ether | 0.0180 | 0.073 |
| methyl acetate | 0.1656 | 0.668 |
| methanol | 0.0087 | 0.035 |
| acetic acid [1] | — | — |

*Normalized results are moles of product divided by moles of allyl methyl ether added.
[1] Not calibrated.

The selectivity of allyl methyl ether to allyl acetate is 64.5 mole percent.

COMPARATIVE EXAMPLE 1

Example 2 is repeated except without any sulfonated polystyrene beads. No allyl acetate is detected by gas chromatograph analysis after 1½ hours. This comparative example demonstrates the effectiveness of sulfonated polystyrene beads as catalyst.

COMPARATIVE EXAMPLE 2

Example 2 is repeated except without any copper (I) chloride. The results of the gas chromatograph analysis of the reactant products are shown in Table III.

TABLE III

| Product | moles | Normalized Results* |
|---|---|---|
| allyl methyl ether | 0.2012 | 0.811 |
| allyl acetate | 0.0053 | 0.021 |
| allyl alcohol | 0.0002 | 0.001 |
| diallyl ether | trace | |
| methyl acetate | 0.0269 | 0.217 |
| acetic acid [1] | — | — |

*Normalized results are moles of product divided by moles of allyl methyl ether added.
[1] Not calibrated.

The selectivity of allyl methyl ether to allyl acetate is 11.1 mole percent. This comparative example demonstrates the effectiveness of the promoter.

EXAMPLE 3

Example 2 is repeated except using 7.24 g (0.1004 mole) of allyl methyl ether, 30.2 g (0.5046 mole) of acetic acid, 1 g (0.0101 mole) of copper (I) chloride, 10 g of sulfonated polystyrene beads and 5 ml (0.04088 mole) of m-xylene. The reactor is heated at 75° C. to 80° C. for 65 minutes and the results of the gas chromatograph analysis of the reaction products are shown in Table IV.

TABLE IV

| Product | moles | Normalized Results* |
|---|---|---|
| allyl methyl ether | 0.0770 | 0.767 |
| allyl acetate | 0.0256 | 0.255 |
| allyl alcohol | 0.0008 | 0.025 |
| diallyl ether | 0.0001 | 0.001 |
| methyl acetate | 0.0388 | 0.387 |
| acetic acid [1] | — | — |

*Normalized results are moles of product divided by moles of allyl methyl ether added.
[1] Not calibrated.

The selectivity of allyl methyl ether to allyl acetate is 91.3 mole percent.

EXAMPLE 4

Example 2 is repeated except using 36 g (0.500 mole) of allyl methyl ether, 60 g (1.000 mole) of acetic acid, 1 g (0.0101 mole) of copper (I) chloride and 10 g of sulfonated polystyrene beads. The reaction is heated at a temperature of 50° C. for 16 hours. The results of the gas chromatograph analysis of the reaction products are shown in Table V.

TABLE V

| Product | moles | Normalized Results* |
|---|---|---|
| allyl methyl ether | 0.4080 | 0.8160 |
| allyl acetate | 0.0870 | 0.1740 |
| allyl alcohol | 0.0041 | 0.0082 |
| diallyl ether | 0.0022 | 0.0044 |
| methyl acetate | 0.1398 | 0.2796 |
| methanol | — | — |

*Normalized results are moles of product divided by moles of allyl methyl ether added.

The selectivity of allyl methyl ether to allyl acetate is 94.5 mole percent.

EXAMPLE 5

The reactor at the end of Example 5 is resealed and heated to a temperature of 75° C. for 4 hours. The results of the gas chromatograph analysis of the reaction products are shown in Table VI.

TABLE VI

| Product | moles | Normalized Results* |
|---|---|---|
| allyl methyl ether | 0.2294 | 0.4588 |
| allyl acetate | 0.2031 | 0.4062 |
| allyl alcohol | 0.0159 | 0.0318 |
| diallyl ether | 0.0106 | 0.0212 |
| methyl acetate | 0.3022 | 0.6044 |
| methanol | 0.0072 | 0.0144 |

*Normalized results are moles of product divided by moles of allyl methyl ether added.

The selectivity of allyl methyl ether to allyl acetate is 75.0 mole percent.

Examples 5 and 6 show that with increased reaction time conversions increase but selectivities decrease for this embodiment of the invention.

EXAMPLE 6

Example 1 is repeated except with 36.76 g (0.510 mole) of allyl methyl ether, 10.68 g (0.1036 mole) of N-methyl ethyl carbamate, 1 g (0.0101 mole) of copper (I) chloride and 10 g of sulfonated polystyrene beads. The reactor is heated for 1 hour to a temperature of 100° C. The results of the gas chromatograph analysis of the reaction products are shown in Table VII.

TABLE VII

| Product | moles | Normalized Results* |
|---|---|---|
| allyl methyl ether | 0.3976 | 0.7796 |
| N—allyl, N—methyl ethyl carbamate | 0.0490 | 0.0961 |
| N—methyl ethyl carbamate | 0.0564 | 0.1106 |
| allyl alcohol [1] | — | — |
| diallyl ether [1] | — | — |
| methanol [1] | — | — |

*Normalized results are moles of product divided by moles of allyl methyl ether added.
[1] Not calibrated.

The selectivity of allyl methyl ether to N-allyl, N-methyl ethyl carbamate is 43.6 mole percent.

EXAMPLE 7

Example 1 is repeated except using 36 g (0.500 mole) of allyl methyl ether, 8.7 g (0.100 mole) of 2-oxazolidinone, 1 g (0.0101 mole) of copper (I) chloride and 10 g of sulfonated polystyrene beads. The reactor is heated to a temperature of 100° C. for 1 hour. The reactor is cooled and the reaction mixture is filtered to remove the 2-oxazolidinone which crystallized at 25° C. The remaining liquid is distilled and N-allyl 2-oxazolidinone is detected boiling at 100° C.–105° C. at 0.8 mm Hg. No quantification of the reaction products is done. Therefore, yields and selectivities are not calculated.

EXAMPLE 8

Example 1 is repeated except using 30 g (0.417 mole) of allyl methyl ether, 7.9 g (0.0050 mole) of benzene sulfonamide, 1 g (0.0101 mole) of copper (I) chloride and 5 g of sulfonated polystyrene beads. The reactor is heated to a temperature of 100° C. for 1 hour. After the reactor is cooled, the reaction mixture is separated by liquid chromatography using as the ambient solvent a solvent mixture containing weight ratios of diethyl ether/cyclohexane/methanol of 4/5/1. Benzene sulfonamide, N-allyl benzene sulfonamide, and N,N-diallyl benzene sulfonamide are detected by infrared and nuclear magnetic resonance spectroscopy.

The product mixture is vacuum distilled at 210° C. at a pressure of 1-2 mm Hg and little product separation occurs. The mixture is diluted with $CH_2Cl_2$ and filtered to remove most benzene sulfonamide leaving 2.8 g of product mixture. This product mixture contains 75-80 weight percent N-allyl benzene sulfonamide and the remainder is N,N-diallyl benzene sulfonamide. The remainder of the products are neither identified nor quantified. Therefore, yields and selectivities are not calculated.

Examples 1-8 demonstrate the invention with various reactants and under various conditions. Comparative Examples 1 and 2 demonstrate the effect of removing the catalyst and promoter independently.

We claim:

1. A process for the formation of $\beta,\gamma$-unsaturated esters, carbamates and sulfonamides wherein no salt is formed which comprises contacting a $\beta,\gamma$-unsaturated non-epoxide ether with an organic compound selected from the group consisting of carboxylic acids, carbamates and sulfonamides in the presence of a catalytic amount of a catalyst; the catalyst containing (1) a sulfonic acid, (2) $BF_3$, (3) $AlCl_3$, (4) $BF_3 \cdot (CH_3CH_2)_2O$, (5) sulfuric acid or (6) a combination thereof; and, in the presence of a promoting amount of a promoter selected from the group consisting of copper (I) salts and cobalt (II) salts under conditions sufficient to form the corresponding $\beta,\gamma$-unsaturated ester, carbamate or sulfonamide.

2. The process of claim 1 in which the promoter is copper (I) chloride.

3. The process of claim 2 in which $\beta,\gamma$-unsaturated non-epoxide ether is an allyl ether.

4. The process of claim 3 in which the allyl ether is allyl methyl ether.

5. The process of claim 1 in which the organic compound is a carboxylic acid.

6. The process of claim 5 in which the carboxylic acid is acetic acid.

7. The process of claim 1 in which the organic compound is a carbamate.

8. The process of claim 1 in which the organic compound is a sulfonamide.

9. The process of claim 1 in which the catalyst is sulfonated polystyrene beads.

10. The process of claim 9 in which the promoter is copper (I) chloride.

11. The process of claim 6 in which the catalyst is sulfonated polystyrene beads and the promoter is copper (I) chloride.

12. The process of claim 11 in which the contact is at a temperature between about 70° C. and about 150° C. at about the generated pressure.

13. The process of claim 10 in which the conversion is at least about 30 percent of the $\beta,\gamma$-unsaturated non-epoxide ether and the selectivity of $\beta,\gamma$-unsaturated ester, carbamate or sulfonamide is at least about 70 mole percent based on the reacted $\beta,\gamma$-unsaturated non-epoxide ether.

14. A process for the salt-free formation of allyl esters, carbamates and sulfonamides which comprises contacting allyl methyl ether with an organic compound selected from the group consisting of carboxylic acids, carbamates and sulfonamides in the presence of a catalytic amount of sulfonated polystyrene beads and a promoting amount of copper (I) chloride under conditions sufficient to form the corresponding allyl ester, allyl carbamate or allyl sulfonamide.

15. The process of claim 14 in which the contact is at a pressure between about 100 psig and about the generated pressure.

16. The process of claim 15 in which the selectivity to allyl ester, allyl carbamate or allyl sulfonamide is at least about 50 mole percent based on the reacted allyl methyl ether.

17. A process for the formation of allyl esters wherein no salt is formed which comprises contacting a non-epoxide allyl ether with an organic carboxylic acid in the presence of a catalytic amount of sulfonated polystyrene beads and a promoting amount of copper (I) chloride under conditions sufficient to form the corresponding allyl ester.

18. The process of claim 17 in which the selectivity to allyl ester is at least about 50 mole percent based on the reacted allyl ether.

* * * * *